United States Patent
Tanaka

(10) Patent No.: US 7,879,359 B2
(45) Date of Patent: Feb. 1, 2011

(54) COMPOSITIONS FOR PREPARING EXTERNAL CARBON DIOXIDE AGENTS

(75) Inventor: Masaya Tanaka, Kobe (JP)

(73) Assignee: Neochemir Inc., Kobe-shi (JP)

( * ) Notice: Subject to any disclaimer, the term of this patent is extended or adjusted under 35 U.S.C. 154(b) by 1569 days.

(21) Appl. No.: 10/474,215

(22) PCT Filed: Apr. 5, 2002

(86) PCT No.: PCT/JP02/03467

§ 371 (c)(1), (2), (4) Date: Apr. 12, 2004

(87) PCT Pub. No.: WO02/080941

PCT Pub. Date: Oct. 17, 2002

(65) Prior Publication Data

US 2004/0219230 A1  Nov. 4, 2004

(30) Foreign Application Priority Data

Apr. 6, 2001 (JP) ............................. 2001-108816
Nov. 12, 2001 (JP) ............................. 2001-346381

(51) Int. Cl.
*A61K 9/14* (2006.01)

(52) U.S. Cl. .................................................... 424/489

(58) Field of Classification Search .................. None
See application file for complete search history.

(56) References Cited

U.S. PATENT DOCUMENTS

| 5,100,674 A | 3/1992 | Ser et al. |
| 5,306,506 A | 4/1994 | Zema et al. |
| 2006/0257504 A1 * | 11/2006 | Tanaka et al. ............... 424/700 |

FOREIGN PATENT DOCUMENTS

| EP | 1043023 | * | 1/2000 |
| EP | 1043023 | A | 10/2000 |
| EP | 1 604 645 | A1 | 12/2005 |
| JP | 61-207322 | A | 9/1986 |
| JP | 2000-319187 | A | 11/2000 |
| JP | 2000-319187 | A | 11/2000 |
| WO | WO 96/19189 | A | 6/1996 |
| WO | WO99/24043 | A1 | 5/1999 |

OTHER PUBLICATIONS

European Search Report, dated Mar. 14, 2007.
International Search Report, Jul. 13, 2009, pp. 1-3.
International Search Report, Jul. 7, 2009, pp. 1-3.

* cited by examiner

*Primary Examiner*—Johann R Richter
*Assistant Examiner*—Kristie L Brooks
(74) *Attorney, Agent, or Firm*—Westerman, Hattori, Daniels & Adrian, LLP

(57) ABSTRACT

Compositions for preparing external carbon dioxide agents comprising a granular material containing a water-soluble acid(s), a thickener(s) and a water-soluble dispersant(s) as the essential components wherein the thickener(s) is (are) mixed with the water-soluble acid(s) and the water-soluble dispersant(s), and a viscous material, which consists of a carbonate(s), water and a thickener(s) as essential components; to be mixed with the said granular material at use, by which an external carbon dioxide agent can be prepared easily in a short period of time. The prepared external carbon dioxide agent, containing much carbon dioxide evenly all over, has sufficient viscosity and can form a coating film on the surface in contact with air, therefore the diffusion of carbon dioxide is suppressed, the applied agent does not droop and its thickness is not reduced when applied to skin or mucosa; and the agent shows potent and quick cosmetic and medical effects.

8 Claims, No Drawings

COMPOSITIONS FOR PREPARING EXTERNAL CARBON DIOXIDE AGENTS

CROSS REFERENCE TO RELATED APPLICATION

This application is a 35 USC §371 National Phase Entry Application from PCT/JP02/03467, filed Apr. 5, 2002, and designating the U.S.

TECHNICAL FIELD

The present invention relates to compositions for preparing external carbon dioxide agents with cosmetic and medical effects.

BACKGROUND ART

It is obvious that cosmetic and medical effects are obtained by transdermally or transmucosally absorbed carbon dioxide, which improves blood circulation of skin, subcutaneous tissue, and muscle, and activates their metabolism. This is widely recognized by the fact that carbon dioxide springs are used to obtain these effects all over the world until now, or by various researches. For example, Hiyoshi et al. have reported that an artificial carbon dioxide spring is effective for an intractable decubitus ulcer (Toshinori Hiyoshi; Effects of Artificial CO2 Bathing in Pressure Sore. Sogo Rehabilitation 17(8): 605-609, 1989).

In order to obtain cosmetic and medical effects easily by external use of carbon dioxide, an external carbon dioxide agent that contains carbon dioxide, or an external carbon dioxide agent in which carbon dioxide is generated at use, have been proposed. An external carbon dioxide agent that contains carbon dioxide has disadvantages of un-establishment of manufacturing technique, and of high cost of their storing containers with no loss or a small loss of carbon dioxide. On the other hand, an external carbon dioxide agent in which carbon dioxide is generated at use is more practical because it does not have such disadvantages. As one of compositions for preparing such an external carbon dioxide agent, for example, a kit preparing for transdermal or transmucosal carbon dioxide absorbing composition is proposed in Japanese Unexamined Patent Publication No. 2000-319187. The said publication shows that the transdermal or transmucousal absorption of carbon dioxide is effective for itching accompanying mucocutaneous diseases or mucocutaneous disorders such as athlete's foot, insect bite, atopic dermatitis, nummular eczema, xeroderma, seborrheic eczema, urticaria, prurigo, housewives' eczema, acne vulgaris, impetigo, folliculitis, carbuncle, furunculosis, phlegmon, pyoderma, psoriasis, ichthyosis, palmoplantar keratoderma, lichen, pityriasis, wound, burn, rhagades, erosion and chilblain; mucocutaneous injuries such as decubitus ulcer, wound, burn, angular stomatitis, stomatitis, skin ulcer, rhagades, erosion, chilblain and gangrene; incomplete takes of skin graft, skin flap, etc.; dental diseases such as gingivitis, alveolar pyorrhea, denture ulcer, nigricans gingiva, stomatitis; skin ulcer, cryesthesia and numbness caused by peripheral circulatory disorders such as thromboangitis obliterans, arteriolosclerosis obliterans, diabetic peripheral circulatory disorder and varicosis in lower extremity; musculoskeletal diseases such as chronic rheumatoid arthritis, cervico-omo-brachial syndrome, myalgia, arthralgia and lumbago; nervous system diseases such as neuralgia, polyarthritis and subcute myelo-optic neuropathy; keratoses such as psoriasis, corn, callosity, ichthyosis, palmoplantar keratoderma, lichen and pityriasis; suppurative dermopathies such as acne vulgaris, impetigo, folliculitis, carbuncle, furunculosis, phlegmon, pyoderma and suppurative eczema; constipation caused by loss of reflection of defecation; suppression of hair re-growth after depilation (treatment of unwanted hair); cosmetic troubles in the skin or hair such as freckles, rough skin, faded skin complexion, loss of skin tension and skin glossiness, and loss of hair glossiness, and local obesities.

The said kit is composed of a combination of a basic material containing water, a thickener and a carbonate and a carbon-dioxide-generating adjuvant containing an acid, or of a combination of an acidic material containing water, a thickener and an acid and a carbon-dioxide-generating adjuvant containing a carbonate. The said kit can prepare an external carbon dioxide agent by mixing each material with its matching carbon-dioxide-generating adjuvant at use. In order to mix each formulation of acid and carbonate and to generate carbon dioxide easily and reliably, viscosity of an acidic or a basic material cannot be high. Accordingly, if an external carbon dioxide agent is prepared from this kit, its viscosity is insufficient and the said agent droops when applied to a vertical part. This drooping has the disadvantage of providing carbon dioxide insufficiently or not at all to the applied part, and to make clothes etc. dirty. Further, since the thickness of the said agent becomes too thin due to its own weight when applied to a horizontal part, there is another disadvantage that enough cosmetic and medical effects are not obtained because the amount of provided carbon dioxide to the applied part is insufficient. If the viscosity of an acidic or a basic material is high to make the said agent has sufficient viscosity, it has further disadvantage that it is hard to mix and dissolve an acidic or a basic material with the corresponding carbon-dioxide-generating adjuvant. Furthermore, even if they are mixed forcibly, carbon dioxide is not sufficiently generated because the carbon-dioxide-generating adjuvant is not sufficiently dissolved. Even if carbon dioxide is generated, an external carbon dioxide agent containing sufficient carbon dioxide cannot be obtained because it takes a long period of time to mix and dissolve carbon-dioxide-generating adjuvant and the generated carbon dioxide diffuses into the air.

Therefore, the said kit cannot avoid using an acidic or a basic material with relatively low viscosity. Accordingly, an external carbon dioxide agent prepared from the said kit is not convenient to use because it droops or is unable to keep necessary thickness when applied onto skin or mucosa. The said agent has to be applied often to obtain desired effect because it cannot supply enough carbon dioxide onto skin or mucosa. For example, the said agent has to be applied everyday for between two weeks and two months to obtain facial slimming effect.

Generally, a thickener in solid stateaggregates when it is directly mixed with water because it slowly swells when contacting with water or slowly dissolves in water. The said aggregate tends to form so-called "DAMA" or "MAMAKO" (dollop) in which solid is contained without water and the outside is covered with dissolved or swelled viscous substance. It takes a long period of time to prepare a viscous material with desired viscosity because water hardly penetrates into the said "DAMA" or "MAMAKO" (dollop) which is covered with the said viscous substance. Although some formulations, which can accelerate dispersion and dissolution of thickeners, are already known, none of such formulation has been known yet about a composition for preparing an external carbon dioxide agent, which can produce an external carbon dioxide agent with high viscosity in a short period of time.

The object of this invention is to provide a composition for preparing an external carbon dioxide agent which can be prepared easily in a short period of time with more potent cosmetic and medical effects in a shorter period of time without making clothes, etc. dirty.

DISCLOSURE OF THE INVENTION

A composition for preparing an external carbon dioxide agent of the present invention comprises a granular material containing a water-soluble acid(s), a thickener(s) and a water-soluble dispersant(s) which is (are) different from the thickener(s) in the said granular material as the essential components wherein the said thickener(s) is (are) mixed with the water-soluble acid(s) and the water-soluble dispersant(s); and a viscous material containing a carbonate(s), water and a thickener(s) as the essential components, which is to be mixed with the said granular material at use; wherein the thickener(s) of the said granular material is (are) one or more selected from the group consisting of processed starch, dextrin, potato starch, corn starch, xanthan gum, and hydroxypropylcellulose; and wherein the water-soluble dispersant(s) of the said granular material is (are) one or more selected from the group consisting of lactose, xylitol, sucrose, D-sorbitol, D-mannitol, and urea (claim 1).

A water-soluble dispersant referred in the present invention is defined as any substance, which easily dissolves in water, and whose particles are stably dispersed in the dispersant and are separated from each other, when mixed with a granular thickener. In addition, a water-soluble acid also acts as a water-soluble dispersant. Besides, a granular material referred in the present invention is defined as solid preparation processed in a granular shape such as a granule, a fine granule, a microcapsule, and the like produced by mixing raw materials. Moreover, an external carbon dioxide agent referred in this invention is defined as an agent for external use, which includes carbon dioxide inside, in order to provide carbon dioxide transdermally or transmucosally by applying to skin or mucosa.

In a composition for preparing an external carbon dioxide agent of the present invention, a viscous material has viscosity that allows a granular material to be mixed or collapsed easily therein.

In a granular material, in which a thickener(s) is (are) mixed with a water-soluble acid(s) and a water-soluble dispersant(s), particles of the thickener(s) are separated from each other by the water-soluble acid(s) and the water-soluble dispersant(s). The said thickener(s), which has (have) granular shape, can dissolve or swell in a short period of time when mixed with a viscous material because the total surface area of the granules of the thickener(s) is large. At this time, the thickener(s) can prevent forming so-called "DAMA" or "MAMAKO" (dollop) because the particles of the said thickener(s), which are separated from each other, dissolve or swell before they aggregate. Further, even though the initial viscosity of a viscous material is not very high, an external carbon dioxide agent with sufficient viscosity can be obtained in a short period of time. Consequently, an external carbon dioxide agent, from which carbon dioxide generated by reaction of a water-soluble acid(s) and a carbonate(s) hardly diffuses into the air, can be obtained easily in a short period of time. Furthermore, the said agent adheres tightly to skin or mucosa with adequate adhesiveness when applied thereto, and the said agent hardly makes cloths etc. dirty, because it hardly droops when applied on a vertical part and hardly becomes thin with its own weight when applied on a horizontal part. Also the said agent is able to provide enough amount of carbon dioxide to the applied part, and more potent cosmetic and medical effects can be obtained in a shorter period of time compared to the prior arts.

In a preferred embodiment of the said composition for preparing an external carbon dioxide agent, the concentration of a water-soluble acid(s) is 2-50% by weight, of a thickener(s) is 10-40% by weight, and of a water-soluble dispersant(s) is 30-85% by weight in the granular material; the concentration of a carbonate(s) is 0.1-10% by weight, and of water is 70-97.5% by weight, and of a thickener(s) is 0.5-20% by weight in the viscous material; and the weight ratio between a granular material and a viscous material is 1:10-40 (Claim 2). In this embodiment, an external carbon dioxide agent having advantages shown below can be prepared. The granular material can be dispersed and collapsed in a short period of time in the viscous material, and the thickener(s) in the granular material quickly dissolves or swells, so that the viscosity of the viscous material is increased in a short period of time. Further, the water-soluble acid(s) and the carbonate(s) react at an adequate rate, so that necessary and enough amount of carbon dioxide can be generated evenly inside the mixture of the said viscous material and the said granular material. The generated carbon dioxide can be effectively absorbed transdermally or transmucosally when applied to skin or mucosa. In addition, an external carbon dioxide agent obtained in this embodiment has sufficient viscosity, so that it will not droop at all even when applied to a vertical part. Further, as the said agent has adequate flexibility and elasticity, it can expand and contract accompanying with the movement of its applied part. Therefore, it may allow a person, whom the said external carbon dioxide agent is applied to, to exercise his or her hand, leg or the like. Furthermore, since the thickness of the said agent applied to a horizontal part is not reduced, and the applied part area does not expand by its own weight, necessary and enough amount of carbon dioxide can be provided certainly at the targeted part only. Therefore, potent cosmetic and medical effects can be obtained in a short period of time.

In another preferable embodiment, the viscous material of a composition for preparing an external carbon dioxide agent contains 1-15% by weight of polyalcohol(s) (Claim 3). An external carbon dioxide agent prepared from the composition for preparing an external carbon dioxide agent stated above is convenient enough for use without other ingredients. However, addition of polyalcohol(s) to the viscous material improves the adhesiveness to skin or mucosa, and elasticity of the prepared external carbon dioxide agent, so that more reliable effects and better usability can be obtained.

In the said composition for preparing an external carbon dioxide agent, it is preferable that the water-soluble acid(s) is (are) one or more selected from the group consisting of citric acid, malic acid, tartaric acid, and sodium dihydrogen phosphate (Claim 4). The above-mentioned acids are widely used as food additives. They are relatively stable chemically, dissolve easily, and react with a carbonate(s) to generate carbon dioxide efficiently.

In the said composition for preparing an external carbon dioxide agent, it is more preferable that the water-soluble acid is malic acid (Claim 5). Citric acid and sodium dihydrogen phosphate tend to become sticky because they are hygroscopic. Therefore, this is the disadvantage in manufacturing efficiency and measure for moisture control of the granular material. Tartaric acid has the disadvantage of not being dissolved easily in cold water. On the other hand, malic acid, especially DL-malic acid is not hygroscopic although it dissolves easily. Therefore, efficiency of producing a granular material using malic acid is high. Malic acid is easy to be stored. And preparing an external carbon dioxide agent with a granular material containing malic acid as the water-soluble acid(s) is easy because it easily dissolves into a viscous material.

In the said composition for preparing an external carbon dioxide agent, it is preferable that the thickener(s) of a viscous material is (are) one or more selected from the group consisting of sodium alginate, propylene glycol alginate, and sodium carboxymethylcellulose (CMC-Na) (Claim 6). Sodium alginate, which is used for a mucus protectant or a wound covering material because of its strong protein affinity, is suitable for the treatment of rough skin or injuries, so it is used preferably for the purpose of the present invention to obtain cosmetic and medical effects. Sodium alginate increases the viscosity of an external carbon dioxide agent additionally or synergistically to the thickener-adding effect of the granular material if the prepared agent is acidic because the viscosity of sodium alginate increases under acidic condition. Therefore, the prepared agent has enough viscosity although the granular material easily dissolves into the viscous material. Also, propylene glycol alginate has the advantages of easy application and good skin or mucosa feeling and it is easy to control viscosity when used as a thickener of a viscous material because its viscosity change by pH change is small. Furthermore, sodium carboxymethylcellulose makes transdermal or transmucosal carbon dioxide absorption of an external carbon dioxide agent more surely because it adds strong adhesiveness to an external carbon dioxide agent even at a low concentration and adhering to skin or mucosa of the said agent can be enhanced. Sodium carboxymethylcellulose also makes carbon dioxide absorption efficiency of an external carbon dioxide agent higher because it easily forms film, which suppresses carbon dioxide diffusion at the air-exposing part of the said agent. With the independent effects of these thickeners, an external carbon dioxide agent prepared from a composition for preparing an external carbon dioxide agent of the present invention shows potent cosmetic and medical effects in a short period of time. Furthermore, with the combined effects of these thickeners, more potent cosmetic and medical effects can be obtained in a shorter period of time.

In the said composition for preparing an external carbon dioxide agent, it is preferable that the thickeners of the said granular material are processed starch, dextrin and potato starch; and the water-soluble dispersant of the said granular material is lactose (Claim 7).

In the said composition for preparing an external carbon dioxide agent, it is preferable that the thickeners of the said granular material are dextrin and corn starch; and the water-soluble dispersant of the said granular material is xylitol (Claim 8).

In the said composition for preparing an external carbon dioxide agent, it is preferable that the thickeners of the said granular material are dextrin and potato starch; and the water-soluble dispersant of the said granular material is lactose (Claim 9).

In the said composition for preparing an external carbon dioxide agent, it is preferable that the thickeners of the said granular material are dextrin and potato starch; and the water-soluble dispersant of the said granular material is sucrose (Claim 10).

In the said composition for preparing an external carbon dioxide agent, it is preferable that the thickener of the said granular material is processed starch; and the water-soluble dispersant of the said granular material is lactose (Claim 11).

In the said composition for preparing an external carbon dioxide agent, it is preferable that the thickener of the said granular material is dextrin; and the water-soluble dispersant of the said granular material is sucrose (Claim 12).

In the said composition for preparing an external carbon dioxide agent, it is preferable that the thickener of the said granular material is potato starch; and the water-soluble dispersant of the said granular material is sucrose (Claim 13).

In the said composition for preparing an external carbon dioxide agent, it is preferable that the thickeners of the said granular material are xanthan gum, dextrin and potato starch; and the water-soluble dispersant of the said granular material is xylitol (Claim 14).

In the said composition for preparing an external carbon dioxide agent, it is preferable that the thickeners of the said granular material are dextrin and hydroxypropylcellulose; and the water-soluble dispersant of the said granular material is D-sorbitol (Claim 15).

In the said composition for preparing an external carbon dioxide agent, it is preferable that the thickeners of the said granular material are dextrin and xanthan gum; and the water-soluble dispersant of the said granular material is D-mannitol (Claim 16).

In the said composition for preparing an external carbon dioxide agent, it is preferable that the thickeners of the said granular material are xanthan gum, dextrin and hydroxypropylcellulose; and the water-soluble dispersant of the said granular material is urea (Claim 17).

BEST MODE FOR CARRYING OUT THE INVENTION

A composition for preparing an external carbon dioxide agent according to the present invention is composed of a granular material and a viscous material. The said granular material is composed of a water-soluble acid(s), a thickener(s), and a water-soluble dispersant(s) as essential components; wherein the thickener(s) is (are) mixed with the water-soluble acid(s) and the water-soluble dispersant(s). Besides, the viscous material is composed of a carbonate(s), water, and a thickener(s) as essential components, and is mixed with the granular material at use.

The viscous material can be in gel, paste, jelly, cream or ointment etc. form, which has the kind of viscosity that when 1 g of the viscous material is applied to a 1 cm diameter circle, which is on the upper end of a glass plate with a length of more than 21 cm and a smooth surface, and when the glass plate is erected on a 60° to the horizontal position, the drooping distance in 5 second is less than 20 cm. However, the viscous material, which droops less than 1 cm after 10 minutes when the glass plate is erected on a vertical position, is not included.

In the said composition for preparing an external carbon dioxide agent, the total percentage of the water-soluble acid(s) and the water-soluble dispersant(s) in the granular material is 32-90% by weight, and the percentage of the water-soluble components is relatively high. Besides, the water content of the viscous material is 70-97.5% by weight, and the percentage is relatively high. Thus, when the granular material and the viscous material are mixed, the water-soluble components are quickly dissolved and the said granular material collapses easily.

In order for the thickener(s) in the granular material to dissolve or swell quickly when in contact with water, it is more preferable that the contact area of the thickener(s) with water is large. Since the smaller the particle size of a thickener(s) is, the larger the total surface area of the thickener(s) is, it is preferable that the shape of the thickener(s) in the granular material is particle, and it is more preferable that the particle size is small. In the granular material, the particles of the thickener(s) are dispersed in both of the water-soluble acid(s) and the water-soluble dispersant(s), which are water-soluble components. Since the said particles are separated from each other by the said water-soluble components, all particles of the thickener(s) quickly dissolve or swell to become viscous substance when in contact with water. Thus, even if the initial viscosity of the said viscous material is not very high, it is possible to prepare an external carbon dioxide agent with sufficient viscosity in a short period of time, without forming "DAMA" or "MAMAKO" (dollop).

In order for the thickener(s) to dissolve or swell quickly, and for the water-soluble acid(s) and the carbonate(s) to react evenly, it is preferable that the thickener(s), the water-soluble acid(s), and the water-soluble dispersant(s) are mixed in the granular material as evenly as possible. Preferably, the water-soluble acid(s) and the water-soluble dispersant(s) are also particles, and more preferably, the particle sizes are small.

In the said composition for preparing an external carbon dioxide agent, the shape of the granular material is not specifically limited, and it can be in the form of granule, fine granule, powder, etc. The granular material can also be in the form of microcapsule, however, granule, fine granule, or powder is more advantageous in terms of manufacturing cost. The granular material is not specifically limited to a particle form, as long as the particle size of the thickener(s) is as fine as possible, and the thickener(s) is (are) mixed with and dispersed in the water-soluble acid(s) and the water-soluble dispersant(s) as evenly as possible. For example, the granular material can be a powder material that is a uniform mixture of the water-soluble acid(s), the water-soluble dispersant(s), and the thickener(s), which are all powder materials. In addition, it can be a granular or a fine granular material, which is made of the said powder materials by adding an appropriate solvent(s) or an appropriate binder(s), etc. In this case, the granules or the fine granules are easy to handle, and since it takes time for the granules or the fine granules to collapse, carbon dioxide generation occurs slowly, the granules or the fine granules are evenly dispersed in the viscous material, carbon dioxide generates evenly in the external carbon dioxide agent and does not diffuse into air, which is preferable. Moreover, depending on the types some thickeners can be used as a binder.

Further, in the said composition for preparing an external carbon dioxide agent, the granular material of very fine powder is not preferable. In that case, carbon dioxide generates quickly and diffuses into air before they are sufficiently mixed with the viscous material. Furthermore, since thickener particles are too close to each other, the thickener particles aggregate and form "DAMA" or "MAMAKO" (dollop) before being dissolved or swelled. Thus, the viscosity of the prepared external carbon dioxide agent is not increased enough, and carbon dioxide does not generated sufficiently and evenly. When the granular materials are in solid form with relatively large volume such as of tablets or capsules, it takes a long period of time for the said granular material to be dissolved and to get the appropriate viscosity for use; furthermore, the generated carbon dioxide does not exist evenly in the external carbon dioxide agent; therefore it is not preferable.

The surface property of the granular material is not specifically limited, but rough surface with a large surface area is preferable in terms of the dissolution rate, and porous surface with high efficiency of water absorption is more preferable. These granular materials can be properly produced by a known granular material producing method, such as a fluid-bed granulation method, an agitating granulation method, a dry crushing granulation method, a wet crushing granulation method, and an extrusion granulation method depending on the property of the ingredients.

In the said composition for preparing an external carbon dioxide agent, the water-soluble acid(s) in the granular material can be one or more selected from a group consisting of organic acids and inorganic acids. The concentration of the acid(s) is preferably 2-50% by weight in the granular material, more preferably 10-35% by weight, and most preferably 15-25% by weight. If the concentration of the acid(s) is less than 2% by weight, generation of carbon oxide is too slow and too little to provide sufficient cosmetic or medical effects. On the other hand, if it is more than 50% by weight, carbon oxide is generated too much and too many bubbles are included in the prepared external agent to make the external agent with appropriate viscosity.

In the said composition for preparing an external carbon dioxide agent, the organic acid(s) used as the water-soluble acid(s) in the granular material can be one or more from the following such as dicarboxylic acids such as oxalic acid, malonic acid, succinic acid, glutaric acid, adipic acid, pimelic acid, fumaric acid, maleic acid, phthalic acid, isophthalic acid, and terephthalic acid; acidic amino acids such as glutamic acid and aspartic acid; and hydroxy acids such as glycolic acid, malic acid, tartaric acid, itatartaric acid, citric acid, isocitric acid, lactic acid, hydroxyacrylic acid, •-oxybutyric acid, glyceric acid, tartronic acid, salicylic acid, gallic acid, tropic acid, ascorbic acid, and gluconic acid.

The inorganic acid(s) can be one or more from the following such as phosphoric acid, potassium dihydrogen phosphate, sodium dihydrogen phosphate, sodium sulfite, potassium sulfite, sodium pyrosulfite, potassium pyrosulfite, acidic sodium hexametaphosphate, acidic potassium hexametaphosphate, acidic sodium pyrophosphate, acidic potassium pyrophosphate, and sulfamic acid. Among these acids, glycolic acid, malic acid, tartaric acid, citric acid, isocitric acid, salicylic acid, sodium dihydrogen phosphate, acidic sodium hexametaphosphate, acidic sodium pyrophosphate, and sulfamic acid are preferable; malic acid, tartaric acid, citric acid, and sodium dihydrogen phosphate are more preferable in terms of usability etc.; and malic acid is most preferable in terms of manufacturing because it is not hygroscopic and easy to handle.

In the said composition for preparing an external carbon dioxide agent, the thickener(s) can be one or more selected from the group consisting of natural polymers, semi-synthetic polymers, synthetic polymers and inorganic compounds.

As natural polymers, one or more from the following, for example, plant-originated polymers such as arabic gum, carrageenan, galactan, agar, quince seed gum, guar gum, tragacanth gum, pectin, mannan, locust bean gum, rice starch, flour starch, corn starch, and potato starch; microbial-originated polymers such as curdlan, xanthan gum, succinoglucan, dextran, hyaluronic acid, and pullulan; and protein polymers such as albumin, casein, collagen, gelatin and fibroin; is (are) used.

As semi-synthetic polymers, cellulose polymers such as ethylcellulose, processed starch, carboxymethylcellulose and its salts, carboxymethylethylcellulose and its salts, carboxymethyl starch and its salts, croscarmellose and its salts, crystallized cellulose, cellulose acetate, cellulose acetate phthalate, hydroxyethylcellulose, hydroxypropyl starch, hydroxypropylcellulose, hydroxypropylmethylcellulose, hydroxypropylmethylcellulose phthalate, powdered cellulose, methylcellulose, and methylhydroxypropylcellulose; starch polymers, such as gelatinized (•-) starch, partially gelatinized (•-) starch, carboxymethyl starch, dextrin, and methyl starch; alginate polymers such as alginic acid, sodium alginate and propylene glycol alginate; and other polysaccharide polymers such as sodium chondroitin sulfate and sodium hyaluronate; may be included and one or more of these is (are) used.

As synthetic polymers, for example, carboxyvinyl polymer, sodium polyacrylate, polyvinylacetaldiethylaminoacetate, polyvinyl alcohol, polyvinyl pyrrolidone, methacrylic acid-ethyl acrylate copolymer, methacrylic acid-ethyl methacrylate copolymer, ethyl methacrylate • trimethylammoniumethyl chloride methacrylate copolymer, dimethylaminoethyl methacrylate-methyl methacrylate copolymer, may be included and one or more of these is (are) used.

As inorganic compounds, for example, hydrated silicon dioxide, light anhydrous silica, colloidal alumina, bentonite and laponite, may be included and one or more of these is (are) used.

In the said composition for preparing an external carbon dioxide agent, as thickeners for the granular material, processed starch, gelatinized (alpha-) starch, carboxymethyl starch, dextrin, xanthan gum, hydroxypropyl cellulose, and polyvinyl pyrrolidone are preferable in terms of the rates of dissolving or swelling; processed starch, dextrin, xanthan gum, hydroxypropyl cellulose, and polyvinyl pyrrolidone are more preferable in terms of usability.

The concentration of the thickener(s) in the granular material is preferably 10-40% by weight, and more preferably 15-35% by weight, and most preferably 20-30% by weight. If the concentration of the thickener(s) in the granular material is less than 10% by, the viscosity of the prepared external agent from the mixture of the granular material and the viscous material is sufficient. On the other hand, if the concentration of the thickener(s) in the granular material is more than 40% by weight %, it takes too long to prepare the external agent because collapsing, dispersing, and dissolving of the granular material are too slow.

In the said composition for preparing an external carbon dioxide agent, the water-soluble dispersant(s) in the granular material is (are) not specifically limited, as long as it is easy to dissolve, chemically stable, and can be used in particular form. For example, starch derivatives, such as gelatinized starch and alpha-cyclodextrin; saccharides such as sucrose, glucose, fructose, saccharose, lactose, xylitol, D-sorbitol, and D-mannitol; polysaccharides such as pullulan and xanthan gum; cellulose derivatives and their salts such as hydroxypropylcellulose, hydroxypropylmethylcellulose, calcium carmellose, and sodium carmellose; synthetic polymers such as polyvinyl pyrrolidone; and urea may be included and one or more of these is (are) used. Among these examples, saccharides and urea are preferable; and xylitol, D-sorbitol, glucose, D-mannitol, fructose, saccharose, lactose, sucrose, and urea are more preferable.

A water-soluble acid works as a water-soluble dispersant, also. However, even if a granular material includes the water-soluble acid(s) and the thickener(s) as essential components, the granular material, without water-soluble dispersant(s) and other water-soluble substance(s) wherein the thickener(s) are mixed with the water-soluble acid(s), the particles of the said thickener(s) are dispersed in the said water-soluble acid(s) and separated each other by the water-soluble acid(s), cannot be used to prepare an external carbon dioxide agent with enough viscosity because the generated carbon dioxide therein diffuses into the air and the thickener(s) forms "DAMA" or "MAMAKO" (dloop) by the progression of the reaction between the acid(s) and the carbonate(s) before the viscosity of the viscous material(s) rises by enough dissolving or swelling of the thickener(s) contact with water, when the said granular material and the viscous material are mixed.

In addition, some water-soluble dispersants can be used as thickeners, and some thickeners can be used as water-soluble dispersants, however, they are considered as different components in the present invention.

In the said composition for preparing an external carbon dioxide agent, carbonates in the viscous material are not specifically limited, as long as they react with an acid to generate carbon dioxide. As a carbonate, for example, ammonium carbonate, ammonium bicarbonate, potassium carbonate, potassium bicarbonate, potassium sesquicarbonate, sodium carbonate, sodium bicarbonate, sodium sesquicarbonate, lithium carbonate, lithium bicarbonate, lithium sesquicarbonate, cesium carbonate, cesium bicarbonate, cesium sesquicarbonate, magnesium carbonate, magnesium bicarbonate, calcium bicarbonate, calcium carbonate, magnesium hydroxide carbonate, and barium carbonate, may be included and one or more of these is (are) used. The concentration of the carbonate(s) in the viscous material is preferably 0.1-10% by weight, and more preferably 0.5-6% by weight, and most preferably 1-3% by weight. If the concentration of the carbonate(s) is less than 0.1% by weight, the amount of carbon dioxide generated is insufficient to provide cosmetic or medical effects, even if the acid(s) is (are) in excess. On the other hand, if the concentration of the carbonate(s) is more than 10% by weight, when mixed with the granular material, which contains chemically equivalent or excessive amount of acid(s), carbon dioxide generated is too much, diffuses into air, and is not used for transdermal or transmucosal absorption. Furthermore, since the thickening effect of the thickener(s) included in the granular material is eliminated by too many bubbles generated inside the prepared external carbon dioxide agent, the external agent is not viscous enough for convenient use, it does not stay on skin or mucosa well, and sufficient cosmetic or medical effects can not be obtained.

In the composition for preparing an external carbon dioxide agent, water for the viscous agent is not specifically limited as long as it can be used for conventional cosmetics, medical supplies, etc., such as distilled water, membrane filtrated water, and ion exchanged water, for example. The concentration of water in the viscous material is preferably 70-97.5% by weight, and more preferably 75-95% by weight, and most preferably 80-92.5% by weight. If the concentration of the water is less than 70% by weight, the viscosity of the viscous material is too high to mix well with the granular material due to lack of flowability, flexibility, and so on, and the granular material cannot be dispersed evenly in the viscous material. In addition to that, the thickener(s) in the granular material does (do) not sufficiently dissolve or swell due to insufficient amount of water, the viscosity is not increased sufficiently and sufficient cosmetic or medical effects can not be obtained. If the concentration of water is more than 97.5% by weight, carbon dioxide generation is too much since the acid(s) dissolves (dissolve) into water too quickly, and carbon dioxide generated diffuses into air as soon as the viscous material is mixed with the granular material. Since carbon dioxide amount in the prepared external agent is too low and the viscosity of the viscous material is not increased sufficiently, sufficient cosmetic or medical effects cannot be obtained. In addition, it is inconvenient to use since the prepared external carbon dioxide agent droops down when it is applied to skin or mucosa.

In the composition for preparing an external carbon dioxide agent, as a thickener(s) in the viscous material, alginate polymers, cellulose polymers, and synthetic polymers are preferable, and sodium alginate, propylene glycol alginate, carboxymethylcellulose and its salts, carboxymethyl starch and its salts, carboxyvinyl polymer, and polyvinyl pyrrolidone are more preferable in terms of usability. Sodium alginate, propylene glycol alginate, and sodium carboxymethylcellulose are most preferable in terms of feel of use.

In the viscous material, the concentration of the thickener(s) is preferably 0.5 to 20% by weight, and more preferably 1 to 10% by weight, and most preferably 2 to 5% by weight. When the concentration of the thickener(s) in the viscous material is less than 0.5% by weight, the viscosity is too low to obtain sufficient viscosity even if the granular material is added. When the concentration of the thickener(s) in the viscous material is more than 40% by weight, the viscosity is too high to be mixed well with the granular material. Even if they are forced to be mixed, since the granular material is not sufficiently decayed, carbon dioxide generation is not sufficient, or carbon dioxide diffuses into air during the long mixing, and it is not effectively used for transdermal or transmucosal absorption, thus, it is difficult to provide sufficient cosmetic or medical effects.

The external carbon dioxide agent obtained from the composition of preparing the external carbon dioxide agent is weakly basic to acidic and not irritant to wounds etc. The hydrogen ion exponent of the external agent is preferably pH 4 to 9 in terms of stimulating action, and more preferably pH 5 to 8.

Although the viscous material in the said composition for preparing an external carbon dioxide agent is convenient enough to use without any additives, addition of polyalcohol(s) can improve the adhesiveness onto skin or mucosa and the elasticity of the external carbon dioxide agent obtained by mixing with the granular material. This improves the ease of use more, and secures the effects more firmly. The concentration of the polyalcohol(s) is preferably 1-15% by weight in the viscous material, and more preferably 3-10% by weight. If the concentration is less than 1% by weight, the said effects cannot be obtained. If the concentration is more than 15% by weight, the viscosity of the said external agent is so low that it flows or droops when applied to skin or mucosa.

A polyalcohol(s) is (are) not specifically limited. Glycols such as ethylene glycol, diethylene glycol, propylene glycol, dipropylene glycol, 1,3-butylene glycol, polyethylene glycol, neopentyl glycol, and spiroglycol; glycerols such as glycerol, diglycerol, and poly glycerol; and diols such as 1,3-butanediol, 1,4-butanediol, 1,6-hexanediol, 1,8-octanediol, and 1,10-decanediol, for example, may be included and one or more of these is (are) used. Among these, 1,3-butylene glycol and glycerol are especially preferable, since they effectively improve adhesiveness and elasticity, give appropriate viscosity, and add moisturizing effect.

Conventionally used material(s) for external agents or cosmetics can be added to the said composition for preparing an external carbon dioxide agent besides the essential components, so far as it (they) does not impair the effects of the present invention. For example, perfumes, dyes, surfactants, oils, moisturizers, alcohols, preservatives, antioxidants, chelating agents, color protection agents, ultraviolet absorbing or reflecting agents, vitamins, amino acids, arbutin, kojic acid, nutrients, anti-inflammatory agents, vasodilators, hormonal drugs, astringents, antihistamines, bactericides, sebum inhibitors, keratin flaking or dissolving agents, anti-seborrhoics, and antipruritic agents may be included. Addition of conventionally used materials helps the external carbon dioxide agent to be used more suitably as cosmetics or external medical treatment agents.

To store the composition for preparing an external carbon dioxide agent of the present invention, the granular material and the viscous material should not be in contact with each other, and preferably are kept in sealed condition. A container to keep the composition is not specifically limited in terms of materials, shapes, structures and so on, and plastics, glass, aluminum, paper, various polymers, and the combination of them for example, can be used as materials. And as to the shape or the structure, a cup, an inner tube, a bag, a bottle, a stick, and a pump can be used. Among these examples, an aluminum stick or an aluminum bag, the interior of which is laminated with polyethylene terephthalate, is especially preferable for the granular material, and an aluminum stick or an aluminum bag, the interior of which is laminated with polyethylene terephthalate, or a cup with a rid, the interior of which is laminated with polyethylene terephthalate, to be heat-sealed, is especially preferable for the viscous material, in terms of sealing, storage stability of the materials, cost for manufacturing and so on.

In the said composition for preparing an external carbon dioxide agent, the granular material and the viscous material can be mixed in appropriate vessels of glass, plastics, etc., or on palm, skin or mucosa, etc. The granular material and the viscous material can be mixed with fingers, etc. or with tools such as a butter knife or a spatula. The granular material can be mixed with the viscous material until it is completely dissolved or until about half of it is dissolved. In the latter case, similar effects to the former case can be obtained because the granular material is being dissolved quickly even it is on skin or mucosa, unless the application period is extremely short.

In the said composition for preparing an external carbon dioxide agent, the amount of viscous material to be mixed with the granular material is preferably 10-40 parts by weight, more preferably 15-35 parts by weight, and most preferably 20-30 parts by weight against 1 part by weight of the granular material. If the viscous material is less than 10 parts by weight against 1 part by weight of the granular material, carbon dioxide generation is so fast and so much, when they are mixed together to prepare the external carbon dioxide agent, that carbon dioxide generated easily diffuses into air, and the viscosity of the obtained external carbon dioxide agent is too low to stick onto skin or mucosa due to too many bubbles inside. Consequently, sufficient cosmetic or medical effects cannot be easily obtained. If the viscous material used is less than 40 parts by weight against 1 part by weight of the granular material, it takes a long period of time for the granular material to be dispersed evenly in the viscous material, carbon dioxide generated during that period tends to diffuse into air, and carbon dioxide generation is insufficient. Consequently, the cosmetic and medical effects are weak.

The external carbon dioxide agent produced from the composition for preparing an external carbon dioxide agent of the present invention should be applied with the thickness of 0.2-10 mm preferably, more preferably 0.5-5 mm, and most preferably 1-3 mm. If the thickness of the applied agent is less than 0.2 mm, it is difficult to generate sufficient cosmetic or medical effects. When more than 10 mm of thickness is difficult to be applied and more potent effects cannot be expected.

For a cosmetic purpose, the application period of the external carbon dioxide agent is preferably five minutes to three hours, and more preferably ten minutes to two hours, and most preferably 15 minutes to one hour. If the application period is less than 5 minutes, the cosmetic effect is weak. More potent effects cannot be expected for more than three hours application period, and the applied skin macerates. For a medical purpose, the application period is similar to that of the cosmetic purpose. For the treatment of a deep wound such as bedsore, etc., continuous application for 24 hours or more is effective as well.

The said composition for preparing an external carbon dioxide agent can prepare an external carbon dioxide agent easily, much carbon dioxide exists evenly all over the prepared external carbon dioxide agent, and the agent has sufficient viscosity and adhesiveness. Further, due to the coating film formed in the part in contact with air, the diffusion of carbon dioxide is suppressed, and the applied agent does not droop, and its thickness is not reduced when it is applied onto skin or mucosa. Therefore, compared with a conventional carbon dioxide external agent, the agent prepared from the present invention is more effective on the following medical and cosmetic areas, and shows effects more quickly; skin and mucosa diseases or itching caused by skin and mucosa diseases such as athlete's foot, insect bite, atopic dermatitis, nummular eczema, xeroderma, seborrheic eczema, urticaria, prurigo, housewives' eczema, acne vulgaris, impetigo, folliculitis, carbuncle, furunculosis, phlegmon, pyoderma, psoriasis, ichthyosis, palmoplantar keratoderma, lichen, pityriasis, wound, burn, rhagades, erosion and chilblain; skin and mucosa injuries such as bedsore, wound, burn, angular stomatitis, stomatitis, skin ulcer, rhagades, erosion, chilblain and gangrene; insufficient engraft of implanted skin and flap; dental diseases such as gingivitis, alveolar pyorrhea, ulcer caused by artificial denture, nigricans gingiva, stomatitis; skin ulcer, psycryesthesia and numbness caused by peripheral circulatory disorders such as thromboangitis obliterans, arteriolosclerosis obliterans, diabetic peripheral circulatory disorder and varices in lower extremity; musculoskeletal diseases such as chronic rheumatoid arthritis, cervico-omo-brachial syndrome, myalgia, arthralgia and lumbago; nerve system diseases such as neuralgia, polyarthritis and subcute myelo-optic neuropathy; keratoses such as psoriasis, corn, callosity, ichthyosis, palmoplantar keratoderma, lichen and pityriasis; suppurative dermopathies such as acne vulgaris, impetigo, folliculitis, carbuncle, furunculosis, phlegmon, pyoderma and suppurative eczema; suppressing hair re-growth after depilation; cosmetic troubles of skin and hair, etc., such as freckles, skin roughness, skin dullness, decline of skin tension and luster, decline of hair luster; or partial obesities.

EXAMPLES

The following descriptions are the examples of the procedure for producing compositions for preparing external carbon dioxide agents according to the present invention. However, it should be noted that the examples are illustrative and the compositions for preparing external carbon dioxide agents according to the present invention are not limited to the descriptions listed below.

Example 1

Producing Granular Material

Porous pillar-shaped granules with the length of approximately 4 mm and the diameter of approximately 1 mm were produced by using 50 parts by weight of lactose as water-soluble dispersant, 30 parts by weight of citric acid as water-soluble acid, 7 parts by weight of processed starch, 3 parts by weight of dextrin and 10 parts by weight of potato starch as thickeners, and water as solvent by wet extrusion granulation method. The yield of this granular material was approximately 60%.

Producing Viscous Material 4.0 parts by weight of sodium hydrogen carbonate as carbonate was dissolved in 91.5 parts by weight of purified water. Then, 1.5 parts by weight of sodium alginate and 3.0 parts by weight of sodium carboxymethylcellulose as thickeners were gradually added and stirred to dissolve while the mixture was warmed up gradually to 60° C. After all materials were dissolved, the mixture was cooled down to room temperature and left to stand overnight to obtain a viscous material.

A composition for preparing an external carbon dioxide agent was obtained by combining a set of the said granular material and the said viscous material.

Example 2

Producing Granular Material

Porous pillar-shaped granules with the length of approximately 4 mm and the diameter of approximately 1 mm were produced by using 65 parts by weight of xylitol as water-soluble dispersant, 15 parts by weight of sodium dihydrogenphosphate as water-soluble acid, 10 parts by weight of dextrin and 10 parts by weight of corn starch as thickeners, and water as solvent by wet extrusion granulation method. The yield of this granular material was approximately 65%.

Producing Viscous Material 1.5 parts by weight of sodium hydrogen carbonate as carbonate, 0.1 part by weight of methylparaben and 1.0 part by weight of phenoxyethanol as preservatives, and 0.1 part by weight of phellodendoron amurense extract, 0.1 part by weight of matricaria extract, 0.1 part by weight of rosewood extract and 0.1 part by weight of Perilla ocymoides extract as other components were dispersed and dissolved in 92.5 parts by weight of purified water. Then, 2.5 parts by weight of sodium alginate and 2.0 parts by weight of sodium carboxymethylcellulose as thickeners were gradually added and stirred to dissolve while the mixture was warmed up gradually to 60° C. After all materials were dissolved, the mixture was cooled down to room temperature and left to stand overnight to obtain a viscous material.

A composition for preparing an external carbon dioxide agent was obtained by combining a set of the said granular material and the said viscous material.

Example 3

Producing Granular Material

Porous pillar-shaped granules with the length of approximately 4 mm and the diameter of approximately 1 mm were produced by using 60 parts by weight of lactose as water-soluble dispersant, 20 parts by weight of citric acid as water-soluble acid, 10 parts by weight of dextrin and 10 parts by weight of potato starch as thickeners, and water as solvent by wet extrusion granulation method. The yield of this granular material was approximately 65%.

Producing Viscous Material 3.0 parts by weight of sodium hydrogen carbonate as carbonate, 3.0 parts by weight of 1,2-pentanediol as preservative, and 0.1 part by weight of mulberry root extract, panax ginseng root extract, Perilla ocymoides extract, Lithospermum officinale extract and rosemary extract as other components were dissolved in 88.5 parts by weight of purified water. Then, 3.0 parts by weight of sodium alginate and 2.0 parts by weight of sodium carboxymethylcellulose, as thickeners were gradually added and stirred to dissolve while the mixture was warmed up gradually to 60° C. After all materials were dissolved, the mixture was cooled down to room temperature and left to stand overnight to obtain a viscous material.

0.7 g of the said granular material was air tightly filled into an aluminum pouch, the interior of which is laminated with polyethylene terephthalate, to give an aluminum stick. 15 g of the said viscous material was air tightly filled into an aluminum pouch, the interior of which is laminated with polyethylene terephthalate. A composition for preparing an external carbon dioxide agent was obtained by combining a set of the said granular material in the said aluminum stick and the said viscous material in the said aluminum pouch.

Example 4

Producing Granular Material

Porous pillar-shaped granules with the length of approximately 4 mm and the diameter of approximately 1 mm were produced by using 50 parts by weight of lactose as water-soluble dispersant, 30 parts by weight of malic acid as water-soluble acid, 7 parts by weight of processed starch, 3 parts by weight of dextrin and 10 parts by weight of potato starch as thickeners, and water as solvent by wet extrusion granulation method. The yield of this granular material was approximately 95%.

Producing Viscous Material 4.0 parts by weight of sodium hydrogen carbonate as carbonate, was dissolved in 91.5 parts by weight of purified water. Then, 1.5 parts by weight of sodium alginate and 3.0 parts by weight of sodium carboxymethyl cellulose as thickeners were gradually added and stirred to dissolve while the mixture was warmed up gradually to 60° C. After all materials were dissolved, the mixture was left to stand overnight and cooled down to room temperature to obtain a viscous material.

A composition for preparing an external carbon dioxide agent was obtained by combining a set of the said granular material and the said viscous material.

Example 5

Producing Granular Material

Porous pillar-shaped granules with the length of approximately 4 mm and the diameter of approximately 1 mm were produced by using 50 parts by weight of lactose as water-soluble dispersant, 20 parts by weight of tartaric acid as water-soluble acid, 10 parts by weight of processed starch, 10 parts by weight of dextrin and 10 parts by weight of potato starch as thickeners, and water as solvent by wet extrusion granulation method. The yield of this granular material was approximately 95%.

Producing Viscous Material 3.0 parts by weight of sodium hydrogen carbonate as carbonate, 3.0 parts by weight of 1,2-pentanediol as preservative, and respective 0.1 part by weight of mulberry root extract, panax ginseng root extract, Perilla ocymoides extract, Lithospermum officinale extract and rosemary extract as other components were dissolved in 88.5 parts by weight of purified water. Then, 3.0 parts by weight of propylene glycol alginate, and 2.0 parts by weight of sodium carboxymethyl cellulose as thickeners were gradually added and stirred to dissolve while the mixture was warmed up gradually to 60° C. After all materials were dissolved, the mixture was left to stand overnight and cooled down to room temperature to obtain a viscous material.

1.5 g of the said granular material was air tightly filled into an aluminum pouch, the interior of which is laminated with polyethylene terephthalate, to give an aluminum stick. 30 g of the said viscous material was air tightly filled to a 50 ml hemisphere-shaped cup of polyethylene terephthalate. An aluminum sheet laminated with polyethylene terephthalate was used to cover the cup by heat sealing. A composition for preparing an external carbon dioxide agent was obtained by combining a set of a stick of the said granular material in the said aluminum stick and a cup of the said viscous material in the said hemisphere-shaped cup.

Example 6

Producing Granular Material

Porous pillar-shaped granules with the length of approximately 4 mm and the diameter of approximately 1 mm were produced by using 73 parts by weight of lactose as water-soluble dispersant, 7 parts by weight of malic acid as water-soluble acid, 7 parts by weight of processed starch, 3 parts by weight of dextrin and 10 parts by weight of potato starch as thickeners, and water as solvent by wet extrusion granulation method. The yield of this granular material was approximately 95%.

Producing Viscous Material 2.0 parts by weight of sodium hydrogen carbonate as carbonate, 1.0 parts by weight of phenoxyethanol as preservative, and 2.0 parts by weight of 1,3-butylene glycol as polyalcohol were dissolved in 90.5 parts by weight of purified water. Then, 1.5 parts by weight of propylene glycol alginate and 3.0 parts by weight of sodium carboxymethyl cellulose as thickeners were gradually added and stirred to dissolve while the mixture was warmed up gradually to 60° C. After all materials were dissolved, the mixture was left to stand overnight and cooled down to room temperature to obtain a viscous material.

A composition for preparing an external carbon dioxide agent was obtained by combining a set of the said granular material and the said viscous material.

Example 7

Porous pillar-shaped granules with the length of approximately 4 mm and the diameter of approximately 1 mm were produced by using 50 parts by weight of sucrose as water-soluble dispersant, 20 parts by weight of malic acid as water-soluble acid, 15 parts by weight of dextrin and 15 parts by weight of potato starch as thickeners, and water as solvent by wet extrusion granulation method. The yield of this granular material was approximately 95%.

3.0 parts by weight of sodium hydrogen carbonate as carbonate, 0.5 part by weight of 1,2-pentanediol as preservative, and 3.0 parts by weight of 1,3-butylene glycol as ployhydric alcohol were dissolved in 89.0 parts by weight of purified water. Then, 1.5 parts by weight of propylene glycol alginate and 3.0 parts by weight of sodium carboxymethyl cellulose as thickeners were gradually added and stirred to dissolve while the mixture was warmed up gradually to 60° C. After all materials were dissolved, the mixture was left to stand overnight and cooled down to room temperature to obtain a viscous material.

A composition for preparing an external carbon dioxide agent was obtained by combining a set of the said granular material and the said viscous material.

Example 8

Producing Granular Material

Porous pillar-shaped granules with the length of approximately 4 mm and the diameter of approximately 1 mm were produced by using 55 parts by weight of lactose as water-soluble dispersant, 25 parts by weight of citric acid as water-soluble acid, 7 parts by weight of processed starch, 3 parts by weight of dextrin and 10 parts by weight of potato starch as thickeners, and water as solvent by wet extrusion granulation method. The yield of this granular material was approximately 65%.

Producing Viscous Material

The viscous material was produced in the same manner as that in Example 2.

A composition for preparing an external carbon dioxide agent was obtained by combining a set of the said granular material and the said viscous material.

Example 9

Producing Granular Material

Porous pillar-shaped granules with the length of approximately 4 mm and the diameter of approximately 1 mm were produced by using 60 parts by weight of lactose as water-soluble dispersant, 25 parts by weight of malic acid as water-soluble acid, 15 parts by weight of processed starch as thickener, and water as solvent by wet extrusion granulation method. The yield of this granular material was approximately 95%.

Producing Viscous Material

The viscous material was produced in the same manner as that in Example 6.

A composition for preparing an external carbon dioxide agent was obtained by combining a set of the said granular material and the said viscous material.

Example 10

Producing Granular Material

Porous pillar-shaped granules with the length of approximately 4 mm and the diameter of approximately 1 mm were produced by using 60 parts by weight of sucrose as water-soluble dispersant, 30 parts by weight of malic acid as water-soluble acid, 10 parts by weight of dextrin as thickener, and water as solvent by wet extrusion granulation method. The yield of this granular material was approximately 95%.

Producing Viscous Material

The viscous material was produced in the same manner as that in Example 6.

A composition for preparing an external carbon dioxide agent was obtained by combining a set of the said granular material and the said viscous material.

Example 11

Producing Granular Material

Porous pillar-shaped granules with the length of approximately 4 mm and the diameter of approximately 1 mm were produced by sufficiently mixing 50 parts by weight of sucrose as water-soluble dispersant, 30 parts by weight of malic acid as water-soluble acid, 20 parts by weight of potato starch as thickener, and water as solvent by wet extrusion granulation method. The yield of this granular material was approximately 95%.

Producing Viscous Material

The viscous material was produced in the same manner as that in Example 6.

A composition for preparing an external carbon dioxide agent was obtained by combining a set of the said granular material and the said viscous material.

Example 12

Producing Granular Material

Porous pillar-shaped granules with the length of approximately 4 mm and the diameter of approximately 1 mm were produced by sufficiently mixing 50 parts by weight of lactose as water-soluble dispersant, 30 parts by weight of malic acid as water-soluble acid, 7 parts by weight of processed starch, 3 parts by weight of dextrin and 10 parts by weight of potato starch as thickeners, and water as solvent by wet extrusion granulation method. The yield of this granular material was approximately 95%.

Producing Viscous Material 4.0 parts by weight of sodium hydrogen carbonate as carbonate was dissolved in 91 parts by weight of purified water. Then, 5 parts by weight of sodium alginate as thickener were gradually added and stirred to dissolve while the mixture was warmed up gradually to 60° C. After all materials were dissolved, the mixture was left to stand overnight and cooled down to room temperature to obtain a viscous material.

A composition for preparing an external carbon dioxide agent was obtained by combining a set of the said granular material and the said viscous material.

Example 13

Producing Granular Material

The granular material was produced in the same manner as that in Example 12.

Producing Viscous Material 4.0 parts by weight of sodium hydrogen carbonate as carbonate was dissolved in 91 parts by weight of purified water. Then, 5 parts by weight of propylene glycol alginate as thickener were gradually added and stirred to dissolve while the mixture was warmed up gradually to 60° C. After all materials were dissolved, the mixture was left to stand overnight and cooled down to room temperature to obtain a viscous material.

A composition for preparing an external carbon dioxide agent was obtained by combining a set of the said granular material and the said viscous material.

Example 14

Producing Granular Material

The granular material was produced in the same manner as that in Example 12.

Producing Viscous Material 4.0 parts by weight of sodium hydrogen carbonate as carbonate was dissolved in 91 parts by weight of purified water. Then, 5 parts by weight of sodium carboxymethyl cellulose as thickener were gradually added and stirred to dissolve while the mixture was warmed up gradually to 60° C. After all materials were dissolved, the mixture was left to stand overnight and cooled down to room temperature to obtain a viscous material.

A composition for preparing an external carbon dioxide agent was obtained by combining a set of the said granular material and the said viscous material.

Example 15

Producing Granular Material

Porous pillar-shaped granules with the length of approximately 4 mm and the diameter of approximately 1 mm were produced by sufficiently mixing 50 parts by weight of xylitol as water-soluble dispersant, 30 parts by weight of malic acid as water-soluble acid, 7 parts by weight of xanthan gum, 5 parts by weight of dextrin, and 8 parts by weight of potato starch as thickeners, and water as solvent by wet extrusion granulation method. The yield of this granular material was about 70%.

Producing Viscous Material 3.0 parts by weight of sodium hydrogen carbonate as carbonate, 0.5 part by weight of 1,2-pentanediol as preservative, 3.0 parts by weight of 1,3-butylene glycol as polyalcohol were dissolved in 89.0 parts by weight of purified water. Then, 1.5 parts by weight of sodium alginate and 3.0 parts by weight of sodium sodium carboxymethyl cellulose as thickener were gradually added and stirred to dissolve while the mixture was warmed up gradually to 60° C. After all materials were dissolved, the mixture was left to stand overnight and cooled down to room temperature to obtain a viscous material.

An external carbon dioxide agent was obtained by combining a set of the said granular material and the said viscous material.

Example 16

Producing Granular Material

Porous pillar-shaped granules with the length of approximately 4 mm and the diameter of approximately 1 mm were produced by sufficiently mixing 50 parts by weight of D-sorbitol as water-soluble dispersant, 20 parts by weight of malic acid as water-soluble acid, 15 parts by weight of dextrin and 15 parts by weight of hydroxypropylcellulose as thickeners, and water as solvent by wet extrusion granulation method. The yield of this granular material was about 65%.

Producing Viscous Material 3.0 parts by weight of sodium carbonate as carbonate, 0.5 part by weight of 1,2-pentanediol as preservative, 3.0 parts by weight of 1,3-butylene glycol as polyalcohol were dissolved in 89.0 parts by weight of purified water. Then, 1.5 parts by weight of propylene glycol alginate and 3.0 parts by weight of sodium carboxymethyl cellulose as thickener were gradually added and stirred to dissolve while the mixture was warmed up gradually to 60° C. After all materials were dissolved, the mixture was left to stand overnight and cooled down to room temperature to obtain a viscous material.

A composition for preparing an external carbon dioxide agent was obtained by combining a set of the said granular material and the said viscous material.

Example 17

Porous pillar-shaped granules with the length of approximately 4 mm and the diameter of approximately 1 mm were produced by sufficiently mixing 45 parts by weight of D-mannitol as water-soluble dispersant, 25 parts by weight of malic acid as water-soluble acid, 15 parts by weight of dextrin and 15 parts by weight of xanthan gum as thickeners, and water as solvent by wet extrusion granulation method. The yield of this granular material was about 90%.

Producing Viscous Material 3.0 parts by weight of sodium hydrogen carbonate as carbonate, 1.0 part by weight of 1,2-pentanediol as preservative, 3.0 parts by weight of 1,3-butylene glycol as polyalcohol were dissolved in 88.5 parts by weight of purified water. Then, 1.5 parts by weight of sodium alginate, and 3.0 parts by weight of sodium carboxymethyl cellulose as thickeners were gradually added and stirred to dissolve while the mixture was warmed up gradually to 60° C. After all materials were dissolved, the mixture was left to stand overnight and cooled down to room temperature to obtain a viscous material.

A composition for preparing an external carbon dioxide agent was obtained by combining a set of the said granular material and the said viscous material.

Example 18

Producing Granular Material

Porous pillar-shaped granules with the length of approximately 4 mm and the diameter of approximately 1 mm were produced by sufficiently mixing 50 parts by weight of urea as water-soluble dispersant, 20 parts by weight of tartaric acid as water-soluble acid, 10 parts by weight of xanthan gum, 10 parts by weight of dextrin, and 10 parts by weight of hydroxypropylcellulose as thickeners, and water as solvent by wet extrusion granulation method. The yield of this granular material was about 95%.

Producing Viscous Material

The viscous material was produced in the same manner as that in Example 7.

1.5 g of the said granular material was air tightly filled into an aluminum pouch, the interior of which is laminated with polyethylene terephthalate, to give an aluminum stick. 30 g of viscous composition was air tightly filled to a 50 ml hemisphere-shaped cup of polyethylene terephthalate. An aluminum sheet laminated with polyethylene terephthalate was used to cover the cup by heat sealing. A composition for preparing an external carbon dioxide agent was obtained by combining a set of a stick of the said granular material in the said aluminum stick and a cup of the said viscous material in the said hemisphere-shaped cup.

Comparative Example 1

Producing Granular Material

Porous pillar-shaped granules with the length of approximately 4 mm and the diameter of approximately 1 mm were produced by using 20 parts by weight of citric acid as water-soluble acid, 30 parts by weight of hydroxypropylcellulose, 20 parts by weight of dextrin and 30 parts by weight of carboxymethyl starch sodium as thickeners by wet extrusion granulation method. The yield of this granular material was about 45%.

Producing Viscous Material 4.0 parts by weight of sodium hydrogen carbonate as carbonate, was dissolved in 91.5 parts by weight of purified water. Then, 1.5 parts by weight of sodium alginate and 3.0 parts by weight of sodium carboxymethyl cellulose as thickeners were gradually added and stirred to dissolve while the mixture was warmed up gradually to 60° C. After all materials were dissolved, the mixture was left to stand overnight and cooled down to room temperature to obtain a viscous material.

A composition for preparing an external carbon dioxide agent was obtained by combining a set of the said granular material and the said viscous material.

Comparative Example 2

The following procedures were based on that of Example 109 in Japanese Unexamined Patent Publication No. 2000-319187.

Producing Granular Material

Porous pillar-shaped granules with the length of approximately 4 mm and the diameter of approximately 1 mm were produced by using 25 parts by weight of citric acid, 25 parts by weight of ethylcellulose, 50 parts by weight of croscarmellose sodium, and water as solvent by wet extrusion granulation method.

Producing Viscous Material 2.4 parts by weight of sodium hydrogen carbonate was dissolved in 89.6 parts by weight of purified water. Then, 4.0 parts by weight of sodium alginate, 2.0 parts by weight of ethylcellulose, and 2.0 parts by weight of sodium carboxymethyl cellulose were gradually added and stirred to dissolve while the mixture was warmed up gradually to 60° C. After all materials were dissolved, the mixture was left to stand overnight and cooled down to room temperature to obtain a viscous material.

A composition for preparing an external carbon dioxide agent was obtained by combining a set of the said granular material and the said viscous material.

Comparative Example 3

Producing Powders Containing Water-Soluble Acid 60 parts by weight of citric acid as water-soluble acid, 20 parts by weight of dextrin and 20 parts by weight of potato starch as thickeners were sufficiently mixed to produce powder. The yield of this granular material was about 100%.

Producing Viscous Material 4.0 parts by weight of sodium hydrogen carbonate as carbonate was dissolved in 91.5 parts by weight of purified water. Then, 1.5 parts by weight of sodium alginate, and 3.0 parts by weight of sodium carboxymethyl cellulose were gradually added and stirred to dissolve while the mixture was warmed up gradually to 60° C. After all materials were dissolved, the mixture was left to stand overnight and cooled down to room temperature to obtain a viscous material.

A composition for preparing an external carbon dioxide agent was obtained by combining a set of the said powders containing water-soluble acid and the said viscous material.

EVALUATION TEST

The compositions for preparing external carbon dioxide agents produced as stated above were evaluated as follows.

Evaluation 1: Effects for Partial Slimming of Face, Skin Whitening, and Skin Beautifying (1)

21 sets of the compositions for preparing an external carbon dioxide agent of Examples 1-18 and Comparative Examples 1-3 were evaluated for ease of preparation. In the evaluation, 1.4 g of the granular material or the powder containing water-soluble acid was mixed with 30 g of the corresponding viscous material from Examples 1-18 and Comparative Examples 1-3 and stirred 30 times in a 5 cm diameter plastic vessel with a spatula to prepare an external carbon dioxide agent.

Subsequently, each 10 g of the prepared external carbon dioxide agent was applied on a subject's right cheek down to the jaw in about 1 mm thickness, and the extent of its drooping down was observed. 15 minutes later, the agent was removed and the condition of the cheek and the skin was observed. The subjects were 21 females of 21 to 42 years old.

The results indicated that it was easy to mix the granular material and the viscous material for preparing an external carbon dioxide agent for all the examples of 1-18, and the granular material evenly dissolved all over the viscous material wherein carbon dioxide was generated sufficiently. Especially, none of the external carbon dioxide agents prepared from these examples drooped down when applied onto subject's cheek. After the agent was removed 15 minutes later, a third party observed the subject's cheek in all cases using the external carbon dioxide agent from the present invention. The third party recognized that the cheek, on which the external carbon dioxide agent was applied, became slimmer, and that the angle of the mouth rose, and that the skin on the cheek became whiter and more transparent compared to the untreated part. Among these examples, the external carbon dioxide agents from Examples 4, 12, 15 and 17 had superior effects for partial slimming of the face, skin whitening, and skin beautifying.

On the other hand, in the case of the composition for preparing an external carbon dioxide agent from Comparative Example 1, it was easy to mix the granular material and the viscous material, and sufficient carbon dioxide was generated. However, the prepared external carbon dioxide agent drooped from the subject's cheek as soon as it was applied and made her clothes dirty. After the said external carbon dioxide agent was removed 15 minutes later, it was observed that her skin became slightly whiter. However, it was not observed that the cheek was slimmed and that the angle of mouth rose.

In the case of the composition for preparing an external carbon dioxide agent from Comparative Example 2, the granular material hardly dissolved in the viscous material, and carbon dioxide was not sufficiently generated. The external carbon dioxide agent prepared from the said composition drooped down from the subject's cheek as soon as it was applied and made her clothes dirty. After the said external carbon dioxide agent was removed 15 minutes later, the granular material remained in the mixture without being dissolved. It was observed that the said agent applied skin became slightly whiter. However, it was not observed that the cheek was slimmed and that the angle of mouth rose, and that her skin became more transparent compared to the untreated cheek.

In the case of the composition for preparing an external carbon dioxide agent from Comparative Example 3, carbon dioxide began to be generated near the surface of the viscous material as soon as the granular material was mixed with the viscous material. Carbon dioxide generation finished before the granular material was well mixed with the viscous material. In addition, "DAMA" or "MAMAKO" (dollop) was produced so much in the viscous material that the granular material could not be dissolved completely. When the external carbon dioxide agent prepared from the said composition was applied to the subject's cheek, "DAMA" or "MAMAKO" still remained. The said agent drooped down from the subject's cheek as soon as it was applied and made her clothes dirty. After the said external carbon dioxide agent was removed 15 minutes later, it was recognized that her skin became slightly whiter. However, it was not recognized that the cheek was slimmed, and that the angle of mouth rose.

Evaluation 2: Effects for Partial Slimming of Face, Skin Whitening, and Skin Beautifying (2)

1.4 g of the granular material and 30 g of the viscous material of a composition for preparing an external carbon dioxide agent in Example 8 and Comparative Example 2, respectively, was mixed and stirred 30 times in a 5 cm diameter plastic vessel with a spatula to prepare an external carbon dioxide agent. 10 g of the external carbon dioxide agent from Example 8 was applied onto a 41-year-old female subjects' right cheek, and 10 g of the external carbon dioxide agent from Comparative Example 2 was applied on her left cheek in approximately 1.5 mm thickness, respectively. Then, the extent of drooping down of each agent was observed. The said agents were removed to observe her cheeks and skin 15 minutes later. The results showed that the external carbon dioxide agent prepared from the composition for preparing an external carbon dioxide agent in Example 8 did not droop down while applied on the subject's right cheek. After it was removed 15 minutes later, a third party observed her cheeks. The third party recognized that her right cheek was slimmed, that the angle of the mouth rose, and that her skin became whiter and more transparent compared to her left cheek. On the other hand, the external carbon dioxide agent prepared from the composition for preparing an external carbon dioxide agent in Comparative Example 2 drooped down as soon as it was applied and made her clothes dirty.

Evaluation 3: Treatment of Wound (1)

An external carbon dioxide agent was prepared from 0.7 g of the granular material and 15 g of the viscous material of the composition for preparing an external carbon dioxide agent in Example 3. 0.5 g of the said agent was applied to a 1 cm cut by hairdressing scissors of the third finger of a 32-year-old male's left-hand and left for 20 minutes. After the same treatment was performed once a day for three days, the wound closed up. If a conventional adhesive bandage is applied, it will take two weeks or more for such cut by hairdressing scissors to close up. Therefore, it is obvious that a composition for preparing an external carbon dioxide agent of the present invention can produce an external carbon dioxide agent with potent wound healing effect.

Evaluation 4: Treatment of Wound (2)

An external carbon dioxide agent was prepared from 0.2 g of the granular material and 3 g of the viscous material of the composition for preparing an external carbon dioxide agent in Example 4. The prepared agent was applied for 15 minutes to a 12 year-old boy's 3 cm by 2 cm shallow skin ulcer, which was an intractable scratched wound with exudate caused by an insect bite. After the same treatment was performed once a day for five days, the wound closed up without side effects.

Evaluation 5: Treatment of Acne

An external carbon dioxide agent was prepared from 0.7 g of the granular material and 15 g of the viscous material of the composition for preparing an external carbon dioxide agent in Example 1. 0.5 g of the said agent was applied for 30 minutes to a reddish acne spot with a height of 1 mm in the center of 29-year-old woman's forehead. After the treatment the said acne became less reddish and smaller. Similarly, 0.5 g of external carbon dioxide agent prepared from the said composition was applied for 30 minutes once a day. The acne completely disappeared four days later.

Evaluation 6: Treatment of Atopic Dermatitis

An external carbon dioxide agent was prepared from 0.7 g of the granular material and 15 g of the viscous material of the composition for preparing an external carbon dioxide agent in Example 6. The prepared agent was applied to the back of the right hand of a 29-year-old male for 30 minutes. The backs of his hands were black-bluish and with many scabs and bleeding caused by atopic dermatitis. This treatment improved the conditions of the black-bluish back of his right hand and made the back of his right hand slightly ruddy, and bleeding stopped. Similarly, the external carbon dioxide agent prepared from 0.7 g of the granular material and 15 g of the viscous material of the composition for preparing an external carbon dioxide agent in Example 6 was applied for 30 minutes every day. On the 12th day, the black color completely disappeared. The skin color turned into a normal skin tone. The number of scabs became fewer than a half of the original numbers. No bleeding was observed at all.

Evaluation 7: Treatment of Pigmentation after Herpes Infection

A 28 year-old female had much pigmentation under her left breast caused by herpes infection. The pigmentation lasted for two weeks or more. An external carbon dioxide agent was prepared from 1.4 g of the granular material and 25 g of the viscous material of the composition for preparing an external carbon dioxide agent in Example 17. The prepared agent was applied to the said female's pigmentation portion, and a synthetic resin film was put on top to cover the agent for 30 minutes. After the same treatment was performed once a day for three weeks, the pigmentation became almost invisible.

Evaluation 8: Treatment of a Nail Bed Defect

A wound covering material was applied to an approximately 0.6 square centimeters nail bed defect, which was caused by a canna, on the left thumb of a 12-year-old male and bleeding almost stopped on the second day. But blood still slightly came out of the defect, and the subcutaneous tissue could be seen. An external carbon dioxide agent was prepared from 0.3 g of the granular material and 5 g of the viscous material of the composition for preparing an external carbon dioxide agent in Example 15. The prepared agent was applied to the said defect to widely cover it and a piece of synthetic resin film was put on top of the agent to cover it for a whole day. The same treatment was repeated. On the fourth day, the newly grown epidermis covered the defect, bleeding stopped completely, and the defect recovered.

These results clearly show that an external carbon dioxide agent can be prepared easily and quickly from a composition for preparing an external carbon dioxide agent of the present invention, and that the prepared external carbon dioxide agent has sufficient viscosity, is easy to apply, and potent cosmetic and medical effects can be obtained in a short period of time.

The invention claimed is:

1. A composition for preparing an external carbon dioxide agent with cosmetic and medical effects comprising:

a granular material containing a water-soluble acid(s), a thickener(s), and a water-soluble dispersant(s), which is (are) different from the thickener(s) in the said granular material as the essential components wherein the said thickener(s) is (are) mixed with the water-soluble acid(s) and the water-soluble dispersant(s);

a viscous material containing a carbonate(s), water and a thickener(s) as the essential components, which is to be mixed with the said granular material at use;

wherein the thickener(s) of the said granular material is (are) one or more selected from the group consisting of processed starch, dextrin, potato starch, corn starch, xanthan gum, and hydroxypropylcellulose;

wherein the water-soluble dispersant(s) of the said granular material is (are) one or more selected from the group consisting of lactose, sucrose, D-mannitol, and urea;

wherein the thickener(s) of the said viscous material is (are) one or more selected from the group consisting of sodium alginate, propylene glycol alginate, sodium carboxymethylcellulose;

wherein the concentration of a water-soluble acid(s) is 2-50% by weight, of a thickener(s) is 10-40% by weight, and of a water-soluble dispersant(s) is 30-85% by weight in the said granular material;

wherein the concentration of a carbonate(s) is 0.1-10% by weight, and of water is 70-97.5% by weight, and of a thickener(s) is 0.5-20% by weight in the said viscous material;

wherein the viscous material contains 1-15% by weight of 1,3-butyleneglycol; and the weight ratio between a granular material and a viscous material is 1:10-40.

2. The composition for preparing an external carbon dioxide agent according to claim 1, wherein the cosmetic effect(s) is (are) prophylaxis and/or improvement of one or more selected from the group consisting of freckles, rough skin, faded skin complexion, loss of skin tension, loss of skin glossiness, loss of hair glossiness, and local obesities.

3. The composition for preparing an external carbon dioxide agent according to claim 1, wherein the medical effect(s) is (are) prophylaxis and/or improvement of one or more selected from the group consisting of:

itching accompanying mucocutaneous diseases or mucocutaneous disorders such as athlete's foot, insect bite, atopic dermatitis, nummular eczema, xerodema, seborrheic eczema, urticaria, prurigo, housewives' eczema, acne vulgaris, impetigo, folliculitis, carbuncle, furunculosis, phlegmon, pyoderma, psoriasis, ichthyosis, palmoplantar keratoderma, lichen, pityriasis, wound, burn, rhagades, erosion and chilblain;

mucocutaneous injuries such as decubitus ulcer, wound, burn, angular stomatitis, stomatitis, skin ulcer, rhagades, erosion, chilblain and gangrene;

incomplete takes of skin graft, skin flap, etc.;

dental diseases such as gingivitis, alveolar pyorrhea, denture ulcer, nigricans gingival, stomatitis;

skin ulcer, cryesthesia and numbness caused by peripheral circulatory disorders such as thromboangitis obliterans, arteriolosclerosis obliterans, diabetic peripheral circulatory disorders and varicosis in lower extremity;

musculoskeletal diseases such as chronic rheumatoid arthritis, cervico-omo-brachial syndrome, myalgia, arthralgia and lumbago;

nervous system diseases such as neuralgia, polyarthritis and subacute myelo-optic neuropathy;

ketatoses such as psoriasis, corn, ichthyosis, palmoplantar keratodema, lichen and pityriasis;

suppurative dermopathies such as acne vulgaris, impetigo, folliculitis, carbuncle, furunculosis, phlegmon, pyoderma and suppurative eczema;

constipation caused by loss of reflection of defecation; and hair re-growth after depilation.

4. A composition of claim 1, wherein the thickener(s) of said granular material is dextrin.

5. A composition of claim 1, wherein the thickener(s) of said granular material is potato starch.

6. A composition of claim 1, wherein said granular material is a granule having a porous surface.

7. A composition of claim 6, wherein the thickener(s) of said granular material is dextrin.

8. A composition of claim 6, wherein the thickener(s) of said granular material is potato starch.

* * * * *